United States Patent
Baba

(10) Patent No.: US 9,823,183 B2
(45) Date of Patent: Nov. 21, 2017

(54) EXTENDING THE RANGE OF TURBIDITY MEASUREMENT USING POLARIMETRY

(71) Applicant: UT-Battelle, LLC, Oak Ridge, TN (US)

(72) Inventor: Justin S. Baba, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 132 days.

(21) Appl. No.: 14/855,307

(22) Filed: Sep. 15, 2015

(65) Prior Publication Data

US 2017/0074780 A1    Mar. 16, 2017

(51) Int. Cl.
 *G01J 4/00* (2006.01)
 *G01N 21/21* (2006.01)
 *G01N 21/51* (2006.01)
 *G01N 21/47* (2006.01)

(52) U.S. Cl.
 CPC ........... *G01N 21/21* (2013.01); *G01J 4/00* (2013.01); *G01N 21/51* (2013.01); *G01N 2021/4769* (2013.01); *G01N 2021/4792* (2013.01)

(58) Field of Classification Search
 CPC ..................................... G01J 4/00; G01J 4/04
 USPC .................................................. 356/364, 369
 See application file for complete search history.

(56) References Cited

U.S. PATENT DOCUMENTS

| | | | |
|---|---|---|---|
| 4,884,886 A * | 12/1989 | Salzman | G01N 21/47 250/225 |
| 5,104,221 A * | 4/1992 | Bott | G01N 15/0211 356/336 |
| 5,515,163 A * | 5/1996 | Kupershmidt | G01N 15/0205 356/338 |
| 5,788,632 A * | 8/1998 | Pezzaniti | G01N 21/21 356/368 |
| 6,118,532 A * | 9/2000 | Peters | G01J 3/4412 356/338 |
| 6,567,166 B2 | 5/2003 | Ottens et al. | |
| 6,721,051 B2 * | 4/2004 | Menguç | G01N 15/0211 356/367 |
| 7,956,998 B2 | 6/2011 | Plant | |
| 8,625,093 B2 * | 1/2014 | Yamaguchi | G01N 15/0205 356/336 |
| 8,654,319 B2 | 2/2014 | Rao et al. | |
| 2009/0059227 A1 * | 3/2009 | Plant | G01N 21/21 356/364 |

(Continued)

OTHER PUBLICATIONS

Ghosh et al., "Mueller matrix decomposition for extraction of individual polarization parameters from complex turbid media exhibiting multiple scattering, optical activity, and linear birefringence," *J. Biomed. Opt.*, 13:044036-1-044036-14 (Aug. 2008).

*Primary Examiner* — Roy M Punnoose
(74) *Attorney, Agent, or Firm* — Klarquist Sparkman, LLP

(57) ABSTRACT

Turbidity measurements are obtained by directing a polarized optical beam to a scattering sample. Scattered portions of the beam are measured in orthogonal polarization states to determine a scattering minimum and a scattering maximum. These values are used to determine a degree of polarization of the scattered portions of the beam, and concentrations of scattering materials or turbidity can be estimated using the degree of polarization. Typically, linear polarizations are used, and scattering is measured along an axis that orthogonal to the direction of propagation of the polarized optical beam.

11 Claims, 3 Drawing Sheets

(56) References Cited

U.S. PATENT DOCUMENTS

2011/0181869 A1\* 7/2011 Yamaguchi ........ G01N 15/0205
356/72
2014/0043609 A1 2/2014 Baba \* cited by examiner

EXTENDING THE RANGE OF TURBIDITY MEASUREMENT USING POLARIMETRY

ACKNOWLEDGMENT OF GOVERNMENT SUPPORT

This invention was made with government support under Contract No. DE-AC05-00OR22725 awarded by the U.S. Department of Energy. The government has certain rights in the invention.

FIELD

This disclosure pertains to turbidity measurement.

BACKGROUND

The measurement of turbidity is useful in assessing samples in a variety of industries. Samples of specimens such as water, foods, fruit juices, and oils can be assessed based on turbidity, and a variety of processes in the brewing, petroleum, pulp and paper and chemical manufacturing industries can be assessed and controlled using turbidity measurements. Turbid samples present several measurement challenges, especially turbid samples having high optical attenuation. Measurement of the very large values of attenuation involved in turbidity measurement is difficult so that differences between highly scattering samples can be hard to quantify. In addition, typical samples can both absorb and scatter an incident measurement beam so that specimen absorption can produce errors in turbidity measurement. Although a wide range of instruments is available for turbidity measurement, alternative measurement approaches are needed, especially for high turbidities.

SUMMARY

According to some examples, apparatus comprise a light source situated to direct a light flux in a first state of polarization (SOP) along first axis and a sample container situated on the first axis so as to receive the light flux. At least one detector is situated along a second axis that is at an angle with respect to the first axis, the detector producing an electrical detection signal in response to a portion of the light flux scattered in the sample container. At least one polarizer is situated along the second axis between the sample container and the detector, wherein the at least one polarizer is oriented so as to produce at least a first electrical detection signal and a second electrical detection signal from the photodetector corresponding to different states of polarization (SOPs) of the portion of the scattered light flux. A processor is coupled to the at least one detector to receive the first and second electrical detection signals and produces an estimate of specimen scattering based on the first and second electrical detection signals. In some examples, the first SOP is a linear SOP and the second axis is perpendicular to a polarization direction associated with the linear SOP. In other examples, the first SOP is a linear SOP and the second axis is parallel to a polarization direction associated with the linear SOP. In still other examples, the first SOP is a circular or elliptical SOP.

In some embodiments, a rotational stage is coupled to rotate the at least one polarizer so as to produce the first and second electrical detection signals, and the first and second electrical detection signals correspond to a maximum and a minimum, respectively. In still other examples, the at least one polarizer includes a first polarizer portion and a second polarizer portion that transmit different SOPs, and the at least one detector comprises a first detector and a second detector situated to receive respective light flux portions from the first and second polarizer portions so as to produce the first and second electrical detection signals. In some examples, the first detector and second detector are detector segments of a common segmented detector.

In representative embodiments, the first SOP is a linear SOP and the at least one polarizer is a linear polarizer. The second axis is perpendicular to the first axis, and the at least one polarizer is oriented so that the first electrical detection signal and the second electrical detection signal correspond to a maximum and a minimum. In this example, the processor produces the estimate of specimen scattering based on a degree of linear polarization based on the first and second electrical detection signals. In further examples, the light source includes a polarizer situated so that the light flux has the first state of polarization and the polarizer is rotatable so as to select the first state of polarization.

Representative methods include directing a light flux in a first state of polarization to a specimen along an input axis and selecting a measurement axis that is at an angle with respect to the input axis and extends from the specimen. A magnitude of a scattered portion of the light flux from the specimen is measured along the axis in at least two states of polarization. Based on the measured magnitudes, an estimate of a specimen's turbidity or a concentration of a material in the specimen is obtained. In other examples, the magnitude of the scattered portion of the light flux from the specimen in two states of polarization is measured so as to determine a maximum and a minimum, and the estimate of the specimen turbidity or the concentration of the material in the specimen is based on the maximum and the minimum. According to other examples, the first state of polarization is a linear SOP and the two states of polarization with which the magnitudes of the scattered portion of the light flux is measured are orthogonal linear SOPs. In still other examples, a linear polarizer is rotated so as to measure the magnitude of the scattered portion of the light flux from the specimen in the at least two states of polarization. In other representative examples, first and second detectors and associated first and second linear polarizers having orthogonal axes are situated so as to measure the magnitudes of the scattered portion of the light flux from the specimen in the at least two states of polarization.

In typical examples, the measurement axis is selected to be orthogonal to the input axis and parallel to a polarization direction associated with the first state of polarization. In other alternatives, the measurement axis is selected to be orthogonal to the input axis and to a polarization direction associated with the first state of polarization. According to other embodiments, the estimate of the specimen turbidity or the concentration of a material in the specimen is based on a degree of linear polarization associated with the magnitude of the scattered portion of the light flux from the specimen in the at least two states of polarization.

According to other examples, apparatus include a laser situated to direct a linearly polarized measurement beam to a specimen and at least one detector situated to produce electrical signals associated with a portion of the linearly polarized input beam scattered by the specimen in orthogonal linear polarizations. A processing system is coupled to the at least one detector so as to produce an estimate of a concentration in a specimen or a turbidity based on the electrical signals.

DETAILED DESCRIPTION

Figure 1:
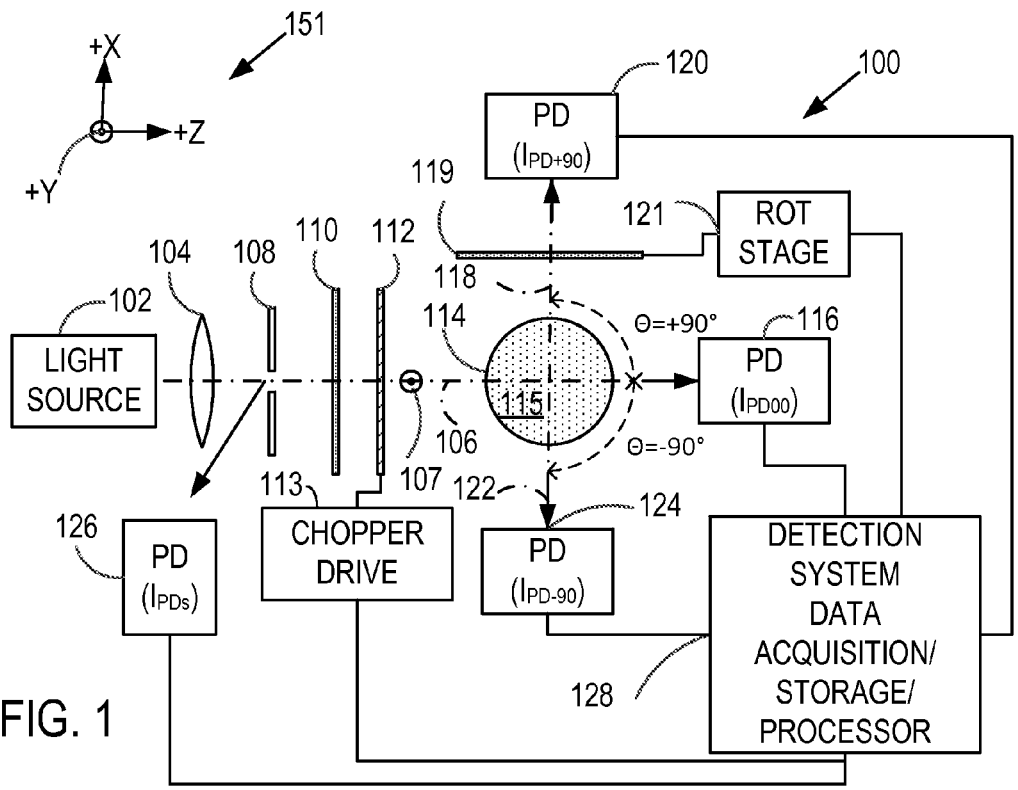
FIG. 1 illustrates a representative polarization-based turbidity measurement system.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections. In some cases, minimum refers to a minimum value or to values that are within 10%, 20%, or 25% of the minimum value. In some cases, maximum refers to a maximum value or to values that are within 10%, 20%, or 25% of the maximum value.

Examples are described with reference to directions indicated as "above," "below," "upper," "lower," and the like. These terms are used for convenient description, but do not imply any particular spatial orientation.

For convenience, beams and light fluxes are described as propagating along one or more axes. Such axes generally are based on one or more line segments so that an axis can include a number of non-collinear segments as the axis is bent or folded or otherwise responsive to mirrors, prisms, lenses, and other optical elements. The term "lens" is used herein to refer to a single refractive optical element (a singlet) or a compound lens that includes one or more singlets, doublets, or other compound lenses. In some examples, beams are shaped or directed by refractive optical elements, but in other examples, reflective optical elements such as mirrors are used, or combinations of refractive and reflective elements are used. Such optical systems can be referred to as dioptric, catoptric, and catadioptric, respectively. Other types of refractive, reflective, diffractive, holographic and other optical elements can be used as may be convenient.

As used herein, a polarized light flux generally has 90% or more (usually much more) of the associated optical power in the selected state of polarization. Angles are generally intended to be specified with about 10 degrees, 5 degrees, 1, degree, or 0.5 degrees and axes referred to as orthogonal can have similar deviations from 90 degrees. In some cases, a final or other polarizer is referred to as an analyzer, if convenient.

As used herein, optical radiation refers to electromagnetic radiation at wavelengths of between about 100 nm and 10 µm, and typically between about 200 nm and 2 µm. In some examples, optical radiation is referred to as one or more beams. For convenience, optical radiation is referred to as light or a light flux in some examples, but need not be at visible wavelengths.

As used herein, optical detectors (generally referred to as detectors herein) produce electrical signals corresponding to an incident light flux. Such electrical signals can be represented as voltages, currents, and as either analog or digital signals. Measurement of an optical signal generally refers to detection of at least a portion of an optical beam with a detector.

Various light sources can be used in the disclosed methods and apparatus such as lasers, light emitting diodes, arc lamps and other lamps. In some cases, such sources produce polarized light fluxes and in such cases, additional polarizers may not be necessary to provide a polarized light flux for specimen measurement. Polarizer orientation can be adjusted by rotation. A waveplate can be used to produce an effective rotation, without rotation of the polarizer. Electrically switchable retarders or other devices such as liquid crystal, Faraday rotator, photoelastic modulator (PEM), or Pockels cells can be used, but are generally omitted from the following description.

Referring to FIG. 1, a turbidity measurement system 100 includes a light source 102 that produces a light flux that is collimated or otherwise shaped by a lens 104 or other single element or multi-element refractive and/or reflective optical system and directed along an axis 106. An aperture 108 is situated to provide additional beam shaping and/or attenuate unwanted light fluxes, and a polarizer 110, such as a linear polarizer, is situated to produce a polarized light flux that is directed along the axis 106 to an optical chopper 112 and to a sample container 114 such as a cylindrical vial as shown in FIG. 1. The optical chopper 112 can be placed prior to the polarizer 110, if desired. A specimen 115 is situated in the sample container 114. The optical chopper 112 is driven by a chopper drive 113 that generally includes a motor assembly so as to rotate the optical chopper to produce an optical modulation to the polarized light flux at a predetermined frequency. A portion of the polarized light flux propagates to a detector 116 that is situated on the axis 106. A first scattered portion of the polarized light flux is received by a polarizer 119, such as a linear polarizer, that is situated along an axis 118 that is at an angle of +90 degrees with respect to the axis 106. The polarizer 119 can be secured to a rotational stage 121. A detector 120 is also situated along the axis 118 so as to receive the first scattered light flux portion after passing through the polarizer 119. A detector 124 is situated along an axis 122 that is at an angle of −90 degrees with respect to the axis 106 so as to receive a second scattered light flux portion. A detector 126 is situated to receive portions of the polarized light flux returned by a sample or a surface of the sample container, such as a specularly reflected portion from a sample vial. The detectors 116, 120, 124, 126, the rotational stage 121 and the chopper driver 113 are coupled to a detection system 128 to permit synchronous detection of the associated light fluxes. Synchronous detection is convenient, but other types of optical detection can be used, such as direct detection. The detection system can also be arranged to produce suitable measurement outputs based on photodetector signals associated with some or all of the detectors 116, 120, 124, 126.

The light source 102 can be a broadband light source such as a lamp, but other light sources such as lasers, laser diodes, and light emitting diodes can be used. Optical power from the light source 102 can be monitored with an additional detector, and some light sources permit direct modulation so that synchronous detection can be used even with the optical chopper 112 omitted. The relative placement of the polarizer 110 and the optical chopper 112 shown in FIG. 1 is one example, but the optical chopper 112 and polarizer 110 can be placed at other locations along the axis 106, or positionally interchanged as may be convenient. The detectors 120, 124 are situated along axes 118, 122, respectively, that are at ±90 degrees with respect to the axis 106. Such an arrangement permits simple analysis, but other angles can be used, and angles of different magnitudes can be used for each of the detectors 120, 124. Typically, angles greater than 45 degrees are preferred. In addition, the description of FIG. 1 generally is based on linear polarization and linear polarizers, but circular or elliptical states of polarization (SOPs) can also be used. Sheet polarizers, dielectric beamsplitter cubes or other dielectric polarizers can be used, or birefringent crystal polarizers such as Glan-Thompson polarizers can be used.

A right handed coordinate systems 151 is shown having a +Y-axis that extends out of the plane FIG. 1. An input linear SOP can be along the +Y-axis as indicated at 107, but other polarization directions can be used having directions specified with reference to the coordinate system 151 or other convenient coordinate system.

The detection system 128 can include one or more lock-in amplifiers, transimpedance amplifiers or other circuitry for processing photosignals from some or all detectors.

Data storage, processing, and control of detector bias, rotational stage positions, chopper operation (such as frequency), control of light source output and amplifier gain can also be controlled with a processor using computer-executable instructions stored in a memory such as RAM or a hard drive. Processors can be implemented as stand-alone or dedicated processors, or provided with a general purpose computer, a laptop, a hand held device, or a tablet computer.

Various detectors such as photodiodes, avalanche photodiodes, photomultipliers or others are suitable, but for ease of description, operation based on photodiodes and the associated photocurrents is described. The detector 116 produces a photocurrent $I_{PD00}$ associated with detection of a ballistic portion of the input polarized light flux that is transmitted by the specimen 115; the detector 120 produces a photocurrent $I_{PD+90}$ associated with detection of a polarized portion of the input polarized light flux as scattered by the specimen 115; the detector 124 produces a photocurrent $I_{PD-90}$ associated with detection of an unpolarized portion of the input polarized light flux as scattered by the specimen. A photocurrent associated with the detector 126 is noted as $I_{PDs}$. The numerous detectors included in the system 100 of FIG. 1 permit various measurement strategies but not all are necessary.

$I_{PD00}$, $I_{PD+90}$, $I_{PD-90}$, and $I_{PDs}$ are used above to refer to photocurrents. However, this notation is used herein to refer to light flux intensities or corresponding electrical signals at or produced by detectors which can be indicated as $PD_{00}$, $PD_{+90}$, $PD_{-90}$, and $PD_s$ for convenience.

Analytical Background

In the following, a representative analytical approach to turbidity determination is provided based on a system such as that of FIG. 1. This approach is representative, and similar approaches based on other SOPs can be used. From FIG. 1, the input intensity to a specimen is redistributed into two detectable components given by:

$$I_0 = \alpha \cdot I_{PD00} + \beta \cdot I_{PD\mp 90}, \quad (1)$$

wherein $\alpha \cdot I_{PD00}$ represents a minimally scattered ballistic component and $\beta \cdot I_{PD\mp 90}$ represents diffusely scattered components. The ballistic component is characterized by the Beer-Lambert Law as:

$$\alpha \cdot I_{PD00} = I_0 \cdot e^{-\tau_t}, \quad (2)$$

wherein $\tau_t$ is an optical density corresponding to loss of the original beam intensity due to both absorption and scatter, i.e., $\tau_t = \tau_a + \tau_s$, respectively. From Eq. (2), the diffuse component therefore consists of all the light scattered out of the original input beam that is not absorbed; this can be written as:

$$\beta_{1,2} \cdot I_{PD\mp 90} = I_0 - \alpha \cdot I_{PD00} = I_0 (1 - e^{-\tau_t}) \cdot e^{-\tau_a}. \quad (3)$$

When polarization is ignored $I_{PD_{-90}}$ is the detected intensity and is captured by detector $PD_{-90}$. When polarization is considered, $I_{PD_{+90}}$ is the detected intensity and is captured by $PD_{+90}$. Eq. (3) is thus separable into two components based on Malus' Law: $I_p$ corresponding to a polarized component (i.e., a component subject to Malus' Law) and $I_d$, a depolarized component (i.e., a component not subject to Malus' Law):

$$\beta_1 \cdot I_{PD+90} = I_t = I_p + I_d. \quad (4)$$

In terms of Malus' Law, Eq. (4) can be rewritten as:

$$I_t(\phi) = \tfrac{1}{2} \cdot \{[1 + P \cdot \cos(2\phi)]|_{max} + [1 + P \cdot \cos(2\phi)]|_{min}\}, \quad (5)$$

wherein P is a degree of polarization and is an azimuthal angle of analyzer orientation with respect to the plane of incidence (i.e., an input SOP) and min and max reference the associated extrema. Note that for an unpolarized light input, in the absence of polarization effects due to scatter, P=0 and therefore $I_t$ lacks a polarization component and is strictly made up of depolarized light, which does not obey Malus' Law. Likewise in the absence of an analyzer in front of a polarization insensitive detector (i.e., for $PD_{-90}$), $$[1 + P \cdot \cos(2\phi)]|_{max} \equiv [1 + P \cdot \cos(2\phi)]|_{min} = k, \quad (6)$$

wherein k is a constant conveying the ensuing polarization insensitivity. From Eq. (4), for normalized intensity, $$I_t = I_p + I_d = 1. \quad (7)$$

$[1 + P \cdot \cos(2\phi)]|_{max}$ and $[1 + P \cdot \cos(2\phi)]|_{min}$ occur for $\phi|_0$ and $\phi|_{90}$, respectively, from Eq. (5). Therefore, $$I_t = I(\phi|_0) + I(\phi|_{90}). \quad (8)$$

Rearranging Eq. (8) to directly map to Eq. (5), yields:

$$I_t = I(\phi|_0) - I(\phi|_{90}) + 2 \cdot I(\phi|_{90}) = I_p + I_d, \quad (9)$$

wherein $I_p = I(\phi|_0) - I(\phi|_{90})$ and $I_d = 2 \cdot I(\phi|_{90})$. Also, note that $$I_p = I(\phi|_0) - I(\phi|_{90}) = [ \quad (10)$$
$$1 + P \cdot \cos(2\phi)]|_{max} - [1 + P \cdot \cos(2\phi)]|_{min} \equiv I_t(\phi)_{range}.$$

The fraction of the detected intensity captured by $PD_{+90}$ that is polarized is the degree of linear polarization (DOLP) and is given by:

$$DOLP = \frac{I_p}{I_t} = \frac{I_p}{I_p + I_d} = \frac{I_t(\phi)|_{range}}{I_t}. \quad (11)$$

However, other functions of the difference between signals associated with different SOPs in the scattered beam can be used. From Eq. (11) it is clear therefore that DOLP is a representative metric for input SOP decorrelation.

Example Implementation

Figure 2:
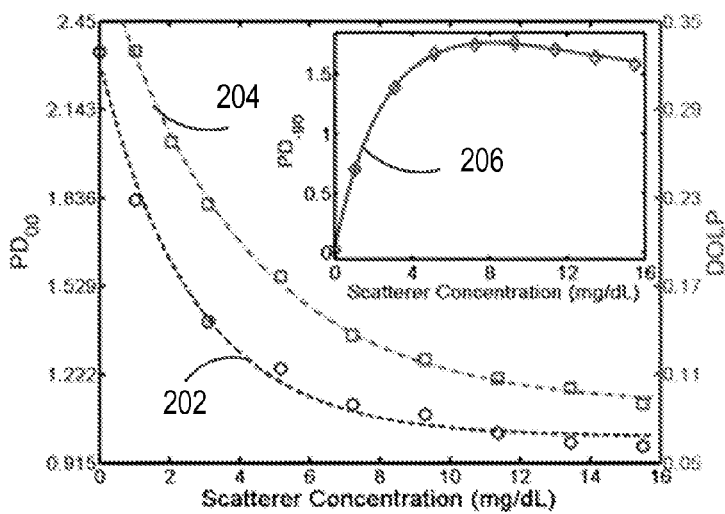
FIG. 2 illustrates measurement results obtained with a system such as shown in FIG. 1.

Representative measurement results are presented for DOLP based on polarization-analyzed detection with $PD_{+90}$ and non-polarized (NP) detection by $PD_{00}$ and $PD_{-90}$ as functions of non-dairy creamer (NDC) concentration, as shown in FIG. 2. Curve 202 illustrates $PD_{00}$ (non-polarized ballistic detection, based on photodetector 116 in FIG. 1) and curve 204 corresponds to DOLP based on polarized detection with a vertical linear (V-SOP) polarized input (based on photodetector 120 in FIG. 1). In FIG. 1, a V-SOP is perpendicular to the plane of the drawing and in a direction of the +Y-axis of the right-handed coordinate system 151 as discussed above. Curve 206 in the embedded plot corresponds to non-polarized detection by $PD_{-90}$ (based on photodetector 124 in FIG. 1) and is a polynomial fit serving to highlight non-monotonic behavior.

For the V-SOP input, note that the ballistic NP-$PD_{00}$ trend closely resembles that of the polarized $PD_{+90}$ detection. Conversely, the NP-$PD_{-90}$ detection mode shows an initial increase with increased NDC scatter concentration and then saturates and proceeds to gradually decrease with increasing NDC concentration. This non-monotonic behavior of NP side scatter detection is anticipated by Eqs. (3) and (4), where:

$$\beta_2 \cdot I_{PD_{-90}} = I_t = I(1 - e^{-\tau_t}) \cdot e^{-\tau_a}, \quad (12)$$

and as sample concentration increases, $\tau_t \to \infty$, thus leading to $e^{-\tau_t} \to 0$. Therefore, $$\beta_2 \cdot I_{PD_{-90}} = I_t = I(1 - e^{-\tau_t}) \cdot e^{-\tau_a} \to I \cdot e^{-\tau_a}, \quad (13)$$

and if $\tau_a \ll 1$, then expanding the exponential function yields, to $1^{st}$ order approximation, $$\beta_2 \cdot I_{PD_{-90}} = I_t \cong I \cdot e^{-\tau_a} \to I(1 - \tau_a) \to I_{sat} \quad (14)$$

Clearly, past the initial saturation point, if $\tau_a$ were to increase with NDC concentration due to greater scatterer agglomeration (a typical consequence of increased scatterer density), then the value of $I_{sat}$ would decrease also as seen in FIG. 2. Alternatively, the results for the polarization fraction show a monotonic exponential relationship with increasing NDC concentration. It is because of this that polarimetric implementation is seen to increase the range of scatterer concentration quantification and by extension turbidity (due to the inverse relationship between turbidity and scattering mean free path). So, whereas turbidity measurement that ignores polarization detection readily saturates (this is the case for the conventional turbidity meter—see the results in Table 1), measurement based on polarimetric implementation continues to show good correlation at higher scatterer concentrations.

The maximal verifiable turbidity measurable in this example was that for the 2.067 mg/mL concentration (784 NTUs). The NP side scatter detection mode was able to quantitate up to 7.233 mg/mL with individual errors <10% for a mean quantification error of 3.91%. Polarization-based detection was able to quantitate up to 13.433 mg/mL with 3.38% mean quantification error. The NP ballistic detection mode quantitated up to 11.367 mg/mL with 11.41% mean quantification error, but individual errors varied greatly and were much higher at just under 19%.

The exponential model inverted to predict concentration C is:

$$y = a_1 \cdot e^{(-a_2 C)} + a_3, \quad (15)$$

wherein y represents either DOLP or NP-intensity The model fit parameters are presented in Table 2 for $R^2 = 0.9984$, 0.9934, and 0.9994 (polarized-DOLP and non-polarized, NP-$PD_{00}$ and -$PD_{-90}$ implementations respectively). Additionally, the models were used to predict the 2.067 mg/mL concentration validation sample with the following respective errors: 5.47%, 22.91%, and 8.07%.

Polarization-based quantitation does not require determining DOLP. In other examples, signals for the analyzer oriented at 0 and 90 degrees (i.e., corresponding to max and min respectively) would be measured. A range of values associated with max/min values for one or more reference samples of known turbidity would be used for calibration so that measured max/min values for a sample could be associated with sample turbidity or concentration using a look up table or other calibration table or curve. In some cases (as noted previously) the two photodiode measurements corresponding to analyzer at 0 and 90 degrees are measure simultaneously. In other examples, the detector 124 in FIG. 1 could be provided with an analyzer having an orientation that is orthogonal to that polarizer 119, or both could be collected with detector 120 via a partitioned analyzer or via switching received SOPs with one or more electrooptic or other devices.

As noted in Table 1, * indicates values of uncertain accuracy as other, slightly larger concentrations (not included in Table 1) also returned the same value. A dagger (†) indicates that the computed mean did not include the value for the concentration 15.500 mg/mL because the associated error was greater than 20%. The values in the second column are in Nephelometric Turbidity Units (NTUs) and were obtained with a conventional turbidity meter. Other indications in Table 1 are: not available due to turbidimeter measurement error message (NA); not calculated (NC) as either outside of a logarithmic range for NP-$PD_{00}$ or that concentration was outside the range that was modeled for NP-PD−90; and predicted (Pred).

TABLE 1

Measurement results.

| Concentration | | P (V-SOP) | | NP-PD$_{00}$ | | NP-PD$_{-90}$ | |
|---|---|---|---|---|---|---|---|
| (mg/mL) | NTUs | Pred. | % Error | Pred. | % Error | Pred. | % Error |
| 1.033 | 383 | 1.006 | 2.63 | 1.23 | 18.81 | 1.01 | 2.29 |
| 2.067 | 784 | — | — | — | — | — | — |
| 3.100 | 1000* | 3.241 | 4.54 | 3.16 | 1.99 | 3.08 | 0.69 |
| 5.167 | NA | 4.996 | 3.30 | 4.57 | 11.47 | 5.59 | 8.27 |
| 7.233 | NA | 7.375 | 1.96 | 6.57 | 9.16 | 7.45 | 3.01 |
| 9.300 | NA | 8.986 | 3.38 | 7.59 | 18.36 | 7.80 | 16.08 |
| 11.367 | NA | 11.044 | 2.84 | 12.35 | 8.68 | NC | NC |
| 13.433 | NA | 12.757 | 5.04 | NC | NC | NC | NC |
| 15.500 | NA | 20.525 | 32.42 | NC | NC | NC | NC |
| Mean | | | †3.38 | | 11.41 | | 6.07 |

TABLE 2

Model fit parameters.

| Coef. | DOLP(V-SOP) Value ± σ | PD$_{00}$ Value ± σ | ‡PD$_{-90}$ Value ± σ |
|---|---|---|---|
| a$_1$ | 0.3115 ± 0.0082 | 1.3020 ± 0.054 | −1.7830 ± 0.0424 |
| a$_2$ | 0.2525 ± 0.0165 | 0.3732 ± 0.042 | 0.4734 ± 0.0328 |
| a$_3$ | 0.0879 ± 0.0045 | 1.0050 ± 0.030 | 1.8030 ± 0.0311 |

In this example, a V-SOP linear polarization input with polarization analysis for detection of the min and max intensity values of side-scatter (i.e., at 90° to the incident propagation direction) was used to measure scattering sample concentration (i.e., turbidity). NDC was used a specimen but other specimens as biological tissues, drinking water, foods, cosmetics, pharmaceuticals and waste water and others can be similarly evaluated.

Additional Examples

Figure 3:
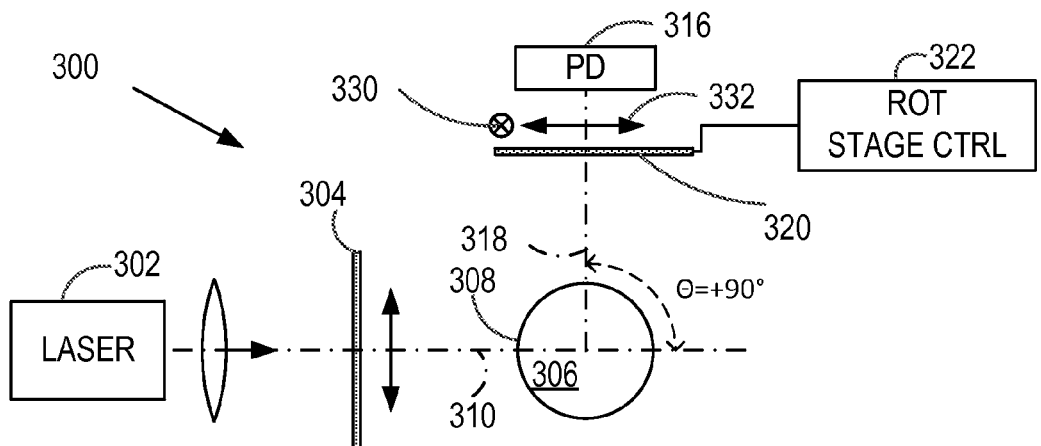
FIG. 3 illustrates a representative system for measuring turbidity.

Referring to FIG. 3, a measurement system 300 includes a laser 302 that directs a measurement beam to a polarizer 304 and then to a specimen chamber 306 defined in a specimen vial 308 that is situated along an axis 310. In this example, the laser 302 produces an unpolarized beam or a weakly polarized beam and the polarizer 304 is oriented so as to produce one or more selected measurement beam SOPs, typically linear SOPs. A detector 316 is situated on an axis 318 that is perpendicular to the axis 310 and scattered portions of the measurement beam are directed to the detector 316 through a rotatable analyzer 320. A stage controller 322 adjusts a rotational angle of the analyzer 320 so that the detector 316 can produce maximum and minimum electrical signals, typically at rotation angles that differ by 90 degrees. In some cases, the maximum and minimum electrical signals are associated with a linear polarization perpendicular to the plane of FIG. 3 (shown as 330) and a linear polarization parallel to the plane of FIG. 3 (shown as 332). The polarizer 304 can be oriented to produce either of these polarizations, or other linear polarizations.

Figure 4:
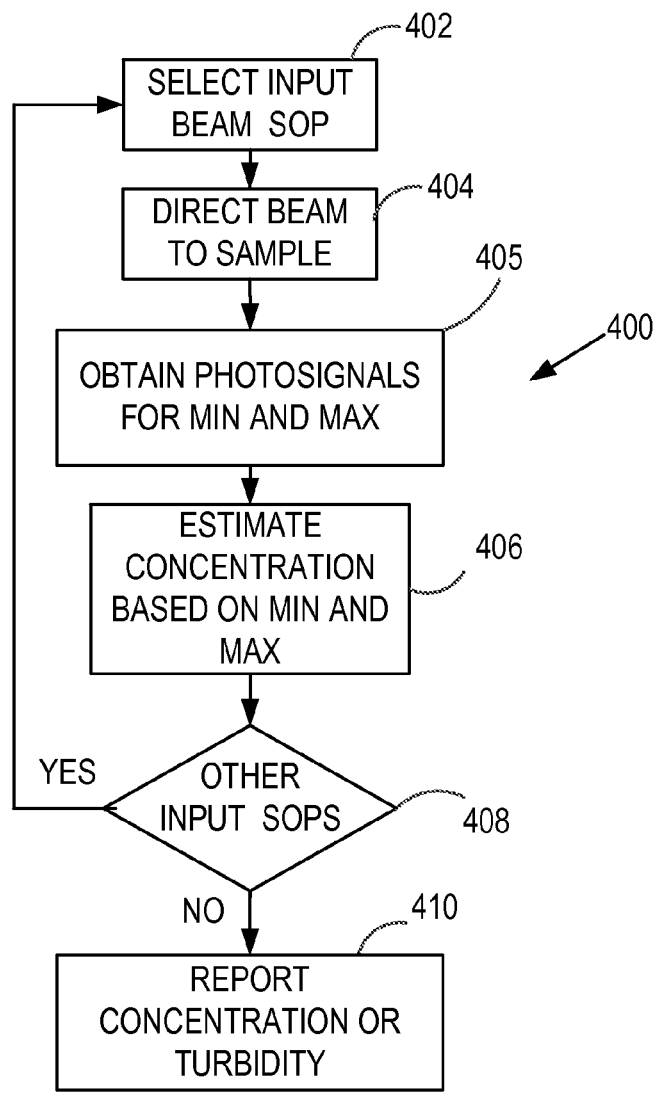
FIG. 4 illustrates a representative method of measuring turbidity.

FIG. 4 illustrates a representative method 400 of measuring turbidity or concentration in a sample. At 402, an input measurement beam SOP is selected and at 402, a measurement beam in this SOP is directed to a sample. At 405, portions of the measurement beam scattered by the sample are detected for SOPs that produce maximum and minimum electrical signals. At 406, a turbidity or concentration estimate is produced based on these electrical signals. At 408, it is determined if additional SOPs are to be used as input SOPs. If not, one or more concentrations or turbidity values are reported at 410.

Figure 5:
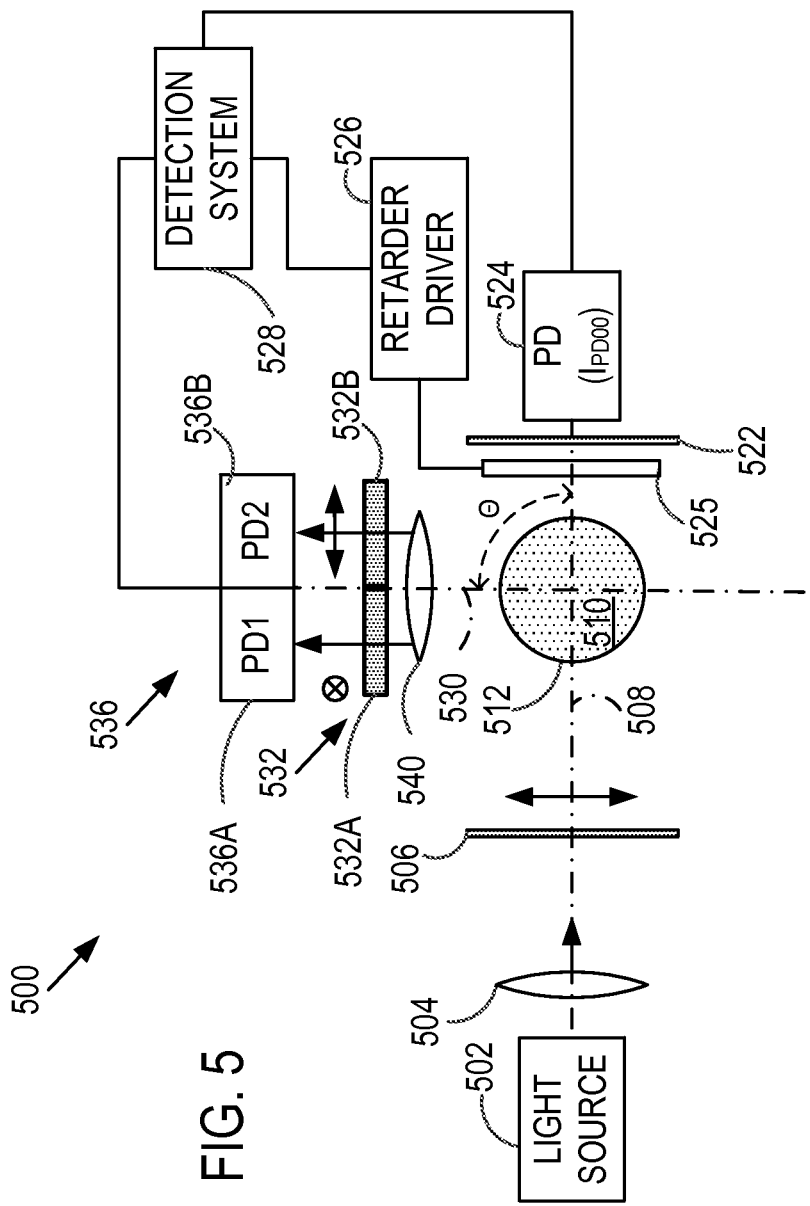
FIG. 5 illustrates an additional representative system for measuring turbidity.

FIG. 5 illustrates a measurement apparatus 500 that includes a light source 502 that emits a light flux that is collected by a lens 504 and directed through a polarizer 506 along an axis 508 to a specimen 510 that is retained in a container 512. A transmitted beam portion is directed to an electrically controllable optical retarder 525 (for example, a liquid crystal or Pockels effect device, or a rotatable retarder) that is coupled to a controller 526 that is used to select a retardation value or orientation. A polarizer 522 is situated to receive the transmitted beam from the retarder 522 and a detector 524 produces an electrical signal associated with the portion transmitted to the detector 524. If desired, maximum and minimum signal values for orthogonal SOPs (in view of the retardance applied by the retarder 52 scan be obtained, and a concentration or turbidity estimate produced by a detection system 528.

A beam portion scattered along a perpendicular axis 530 is directed to a polarizer assembly 532 that contain polarizer segments 532A, 532B associated with orthogonal SOPs. A detector assembly 536 has detectors 536A, 536B that are situated to receive scattered beam portions from the polarizer segments 532A, 532B, respectively. The detection system 528 can use the electrical signals from the detectors 536A, 536B to produce concentration or turbidity estimates. The detector 536 can be a segmented detector, or two or more individual detectors can be used. The polarizer segments 532A, 532B typically are polarizers having different orientations, and fixed into a common assembly. In some cases, a single polarizer can be used an provide with a ½ wave retarder on an input side, wherein the ½ wave retarder is oriented at 45 degrees with respect to the polarization axis of the single polarizer. In either case, measurements that are effectively at two orthogonal directions are obtained. A lens 540 can be used so that scattered beam portions are directed to each of the detectors 536A, 536B.

As shown in this example, polarization based measurement can use either or both of the axes 508, 530, or an axis or axes at angles between 0 and 180 degrees, or 0 and 90 degrees. The light source can be a broadband source, a source that comprises a plurality spectral lines, and spectral filters can be used to select a spectral region of interest.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. I claim all that is encompassed by the appended claims.

I claim:

1. An apparatus, comprising:
   a light source situated to direct a light flux in a first state of polarization (SOP) along first axis;
   a sample container situated on the first axis so as to receive the light flux;
   at least one detector situated along a second axis that is at an angle with respect to the first axis, the detector producing an electrical detection signal in response to a portion of the light flux scattered in the sample container;
   at least one polarizer situated along the second axis between the sample container and the detector, wherein the at least one polarizer is oriented so as to produce at least a first electrical detection signal and a second electrical detection signal simultaneous from the photodetector corresponding to different states of polarization of the portion of the scattered light flux; and a processor that produces an estimate of specimen scattering based on the first and second electrical detection signals.

2. The apparatus of claim 1, wherein the first SOP is a linear SOP and the second axis is perpendicular to a polarization direction associated with the linear SOP.

3. The apparatus of claim 2, wherein the first SOP is a linear SOP and the second axis is parallel to a polarization direction associated with the linear SOP.

4. The apparatus of claim 1, wherein the first SOP is a circular SOP.

5. The apparatus of claim 1, further comprising a rotational stage coupled to rotate the at least one polarizer so as to produce the first and second electrical detection signals.

6. The apparatus of claim 1, wherein the first and second electrical detection signals correspond to a maximum and a minimum, respectively.

7. The apparatus of claim 1, wherein the at least one polarizer includes a first polarizer portion and a second polarizer portion that transmit different SOPs, and the at least one detector comprises a first detector and a second detector situated to receive respective light flux portions from the first and second polarizer portions so as to produce the first and second electrical detection signals.

8. The apparatus of claim 7, wherein the first detector and second detector are detector segments.

9. An apparatus, comprising:
a light source situated to direct a light flux in a first state of polarization (SOP) along first axis;
a sample container situated on the first axis so as to receive the light flux;
at least one detector situated along a second axis that is at an angle with respect to the first axis, the detector producing an electrical detection signal in response to a portion of the light flux scattered in the sample container;
at least one polarizer situated along the second axis between the sample container and the detector, wherein the at least one polarizer is oriented so as to produce at least a first electrical detection signal and a second electrical detection signal from the photodetector corresponding to different states of polarization of the portion of the scattered light flux; and
a processor that produces an estimate of specimen scattering based on the first and second electrical detection signals, wherein the first SOP is a linear SOP, the at least one polarizer is a linear polarizer, the second axis is perpendicular to the first axis, the at least one polarizer is oriented so that the first electrical detection signal and the second electrical detection signal correspond to a maximum and a minimum, and the processor produces the estimate of specimen scattering based on a degree of linear polarization based on the first and second electrical detection signals.

10. The apparatus of claim 1, wherein the light source includes a polarizer situated so that the light flux has the first state of polarization.

11. The apparatus of claim 10, wherein the polarizer is rotatable so as to select the first state of polarization.

* * * * *